(12) United States Patent
Murray, III

(10) Patent No.: US 6,964,681 B2
(45) Date of Patent: Nov. 15, 2005

(54) FLARED STENT AND METHOD OF USE

(75) Inventor: Robert Murray, III, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 383 days.

(21) Appl. No.: 10/060,206

(22) Filed: Jan. 29, 2002

(65) Prior Publication Data

US 2003/0144724 A1    Jul. 31, 2003

(51) Int. Cl.$^7$ ................................................ A61F 2/06
(52) U.S. Cl. ..................................... 623/1.15; 606/108
(58) Field of Search ............................. 623/1.11, 1.15, 623/1.12, 1.13, 1.17, 1.2, 1.31; 606/108, 606/195, 198, 194

(56) References Cited

U.S. PATENT DOCUMENTS

| | | | |
|---|---|---|---|
| 4,413,989 A | 11/1983 | Schjeldahl et al. | |
| 4,878,906 A * | 11/1989 | Lindemann et al. | ....... 623/3.18 |
| 4,896,670 A | 1/1990 | Crittenden | |
| 5,304,199 A | 4/1994 | Myers | |
| 5,383,892 A | 1/1995 | Cardon et al. | |
| 5,562,725 A * | 10/1996 | Schmitt et al. | ............. 623/1.53 |
| 5,575,818 A | 11/1996 | Pinchuk | |
| 5,591,195 A * | 1/1997 | Taheri et al. | .............. 623/1.11 |
| 5,669,924 A | 9/1997 | Shaknovich | |
| 5,720,735 A | 2/1998 | Dorros | |
| 5,741,333 A | 4/1998 | Frid | |
| 5,749,825 A | 5/1998 | Fischell et al. | |
| 5,755,771 A | 5/1998 | Penn et al. | |
| 5,824,053 A | 10/1998 | Khosravi et al. | |
| 5,827,321 A * | 10/1998 | Roubin et al. | .............. 623/1.16 |
| 5,907,893 A | 6/1999 | Zadno-Azizi et al. | |
| 5,938,697 A | 8/1999 | Killion et al. | |
| 5,957,949 A * | 9/1999 | Leonhardt et al. | ......... 623/1.24 |
| 6,010,530 A | 1/2000 | Goicoechea | |
| 6,022,359 A | 2/2000 | Frantzen | |
| 6,059,822 A | 5/2000 | Kanesaka et al. | |
| 6,129,738 A | 10/2000 | Lashinski et al. | |
| 6,143,014 A * | 11/2000 | Dehdashtian et al. | ....... 606/192 |
| 6,241,760 B1 | 6/2001 | Jang | |
| 2001/0011179 A1 | 8/2001 | Adams | |
| 2001/0012943 A1 | 8/2001 | Shaolian et al. | |
| 2001/0029397 A1 | 10/2001 | Thompson | |
| 2002/0052643 A1 | 5/2002 | Wholey et al. | |

FOREIGN PATENT DOCUMENTS

| | | |
|---|---|---|
| EP | 0861638 A2 | 2/1998 |
| EP | 0857471 A2 | 12/1998 |
| FR | 2767673 | 5/1999 |

(Continued)

*Primary Examiner*—Julian W. Woo
*Assistant Examiner*—Victor Nguyen

(57) ABSTRACT

A tubular stent that uniformly scaffolds vessel tissue within a region that significantly changes diameter or transverse dimension. The invention may be practiced in lumens that taper in either retrograde or antegrade directions, and the transverse dimensional change may be relatively linear or flared. A catheter for delivering the stent of the invention may include a balloon having a comparably flared shape and an inverse conical distal end. This abstract is provided to comply with the rules requiring an abstract which will allow a searcher or other reader to quickly ascertain the subject matter of the technical disclosure. It is submitted with the understanding that it will not be used to interpret or limit the scope or meaning of the claims. 37 CFR 1.72(b).

4 Claims, 2 Drawing Sheets

FOREIGN PATENT DOCUMENTS

| WO | WO 97/25002 A1 | 7/1997 |
| WO | WO 00/27307 A1 | 5/2000 |
| WO | WO 00/51523 A1 | 9/2000 |
| WO | WO 01/39699 A1 | 6/2001 |
| WO | WO 02/05729 A2 | 1/2002 |

* cited by examiner

US 6,964,681 B2

FLARED STENT AND METHOD OF USE

FIELD OF THE INVENTION

The invention relates generally to a stent for use in a flared or tapered portion of a body vessel and, more particularly, to a stent for use proximally adjacent a carina in a bifurcation.

BACKGROUND OF THE INVENTION

Stenosis is a narrowing or constriction of a duct or canal. A variety of disease processes, such as atherosclerotic lesions, immunological reactions, congenital abnormalities and the like, can lead to stenoses of arteries or ducts. In the case of stenosis of a coronary artery, this typically leads to myocardial ischemia. Percutaneous transluminal coronary angioplasty (PTCA), the insertion and inflation of a balloon catheter in a coronary artery to affect its repair, is widely accepted as an option in the treatment of obstructive coronary artery disease. In general, PTCA is used to increase the lumen diameter of a coronary artery that is partially or totally obstructed by a build-up of cholesterol fats or atherosclerotic plaque. In PTCA, a coronary guiding catheter provides a channel from outside the patient to the ostium of a coronary artery. Then, a balloon catheter is advanced over a small diameter, steerable guidewire through the guiding catheter, into the artery, and across the stenosis. The balloon is inflated to expand the narrowing. Dilatation of the occlusion, however, can form flaps, fissures and dissections which threaten abrupt reclosure of the dilated vessel or even perforations in the vessel wall. To treat or prevent such sequelae, tubular stents are often placed within the angioplasty site to scaffold the vessel lumen. Stenting in bifurcation stenoses requires specialized implants and delivery equipment to achieve continuous tissue support throughout the complicated three-dimensional anatomy.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

Figure 1:
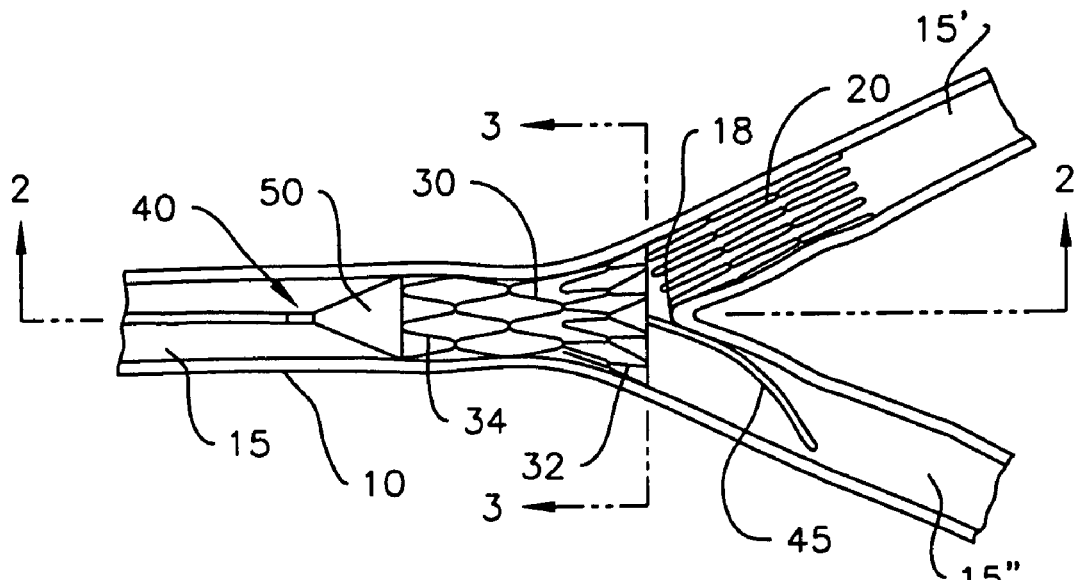
FIG. 1 is a plan view, partially in section, showing a stent according to the invention being implanted adjacent a bifurcation in the lumen of a body vessel.

The present invention is embodied in a tubular stent that effectively scaffolds vessel tissue within a region that significantly changes diameter or transverse dimension. The invention may be practiced in lumens that taper in either retrograde or antegrade directions, and the transverse dimensional change may be relatively linear (frusto-conical) or flared (bell-shaped). FIG. 1 illustrates the invention applied in a bifurcated section of body vessel 10, which has lumen 15 dividing into lumens 15' and 15" at saddle-shaped ridge, or carina 18. Lumen 15' is shown with conventional stent 20 placed therein. Inventive stent 30 is shown in lumen 15 proximally adjacent carina 18, where it is being deployed by catheter 40. Catheter 40 is slidably movable over guidewire 45, and includes balloon 50. Bifurcation stenting typically includes providing scaffold support in all three lumens, 15, 15' and 15". Another stent 20, which would be placed in lumen 15", has been omitted for clarity. When separate stents are implanted in a bifurcated vessel, branch lumens 15', 15" may be stented first, followed by placement of a stent in main lumen 15, as shown in FIG. 1. Alternatively, main lumen 15 may be stented first, then stents may be passed through stented main lumen 15 for deployment in branch lumens 15', 15".

Figure 3:
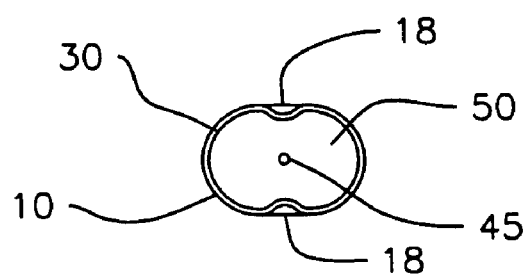
FIG. 3 is a transverse sectional view taken on line 3—3 of FIG. 1.

As shown in FIG. 1, lumen 15 is flared immediately adjacent carina 18. Arteries, such as vessel 10, typically have a gradually tapering diameter in the antegrade direction, as the blood flow requirements naturally decline from their proximal origin to their distal capillary beds. Exceptions to antegrade tapering include bifurcations, wherein the transverse dimension of a vessel flares, or becomes larger, just before a division occurs. The cross-section shown in FIG. 3 illustrates that, in the case of bifurcations, vessel flaring is not radially symmetrical. Lumen 15 expands in a direction across the ostia of lumens 15', 15" without enlarging perpendicular thereto, thus forming a generally oval transverse section. In FIG. 1, stent 30 is shown deployed in vessel 15 with distal end 32 expanded to a dimension larger than proximal end 34. Despite this difference in expanded dimensions, stent 30 provides substantially uniform scaffolding over its length, as will be described in further detail below.

Tubular stents feature a pattern of open cells surrounded by filaments. The filaments may be metallic or polymeric material, as is well known to those of skill in the art of stents. For a stent portion of interest, the filament-to-tissue ratio, termed pattern density, may be calculated by dividing the total area of the stent portion by the area of the filaments within the portion. As the stent transforms from a radially compressed configuration to a radially expanded configuration, the open areas and total stent area expand while the filament area remains generally constant because the total solid volume of the device is unchanging. Therefore, pattern density decreases with expansion of the stent.

Figure 4:
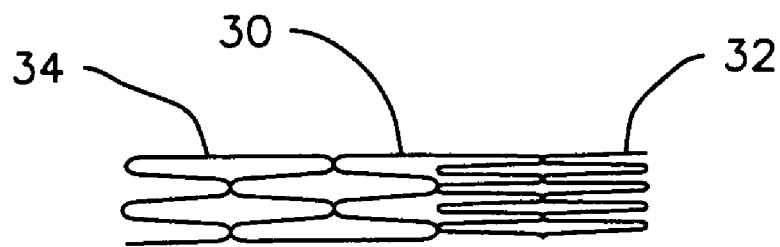
FIG. 4 is an elevation view of a stent according to the invention, shown in a compressed configuration.
Figure 5:
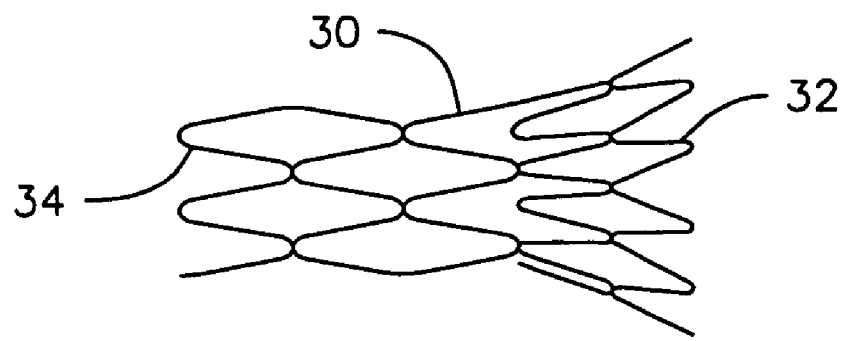
FIG. 5 is an elevation view of a stent according to the invention, shown in an expanded configuration.

FIG. 4 shows stent 30 in a generally cylindrical compressed configuration, which is an example for mounting stent 30 about a delivery catheter such as catheter 40. In the compressed configuration, the pattern density at stent distal end 32 is greater than the pattern density at stent proximal end 34. In the expanded configuration, as shown in FIG. 5, the pattern density at stent distal end 32 is generally equal to the pattern density at stent proximal end 34. The result is relatively uniform pattern density over an expanded stent that has, from end-to-end, a nonuniform transverse dimension.

In the example of stent 30, the tubular body comprises a series of cylindrical hoop elements, each hoop element having a serpentine filament forming a number of proximally and distally facing crowns disposed about the circumference thereof. Each hoop element is axially coupled to an adjacent hoop element through one or more adjoining crowns, depending on the desired balance between structural integrity and bending flexibility. In stent examples employing serpentine filaments, such as stent 30, hoop elements that have differing pattern densities will also have differing crown counts. If it is desired to couple adjacent hoops having differing pattern densities through more than one abutting crown, the crown counts need to have a common denominator of two or more to maintain radial symmetry of the structure. For example, a ten-crown hoop can be joined to a fourteen-crown hoop through two adjoining crowns, spaced 180° apart. In another example, a twelve-crown hoop can be joined to a nine-crown hoop through three adjoining crowns spaced 120° apart.

Figure 2:
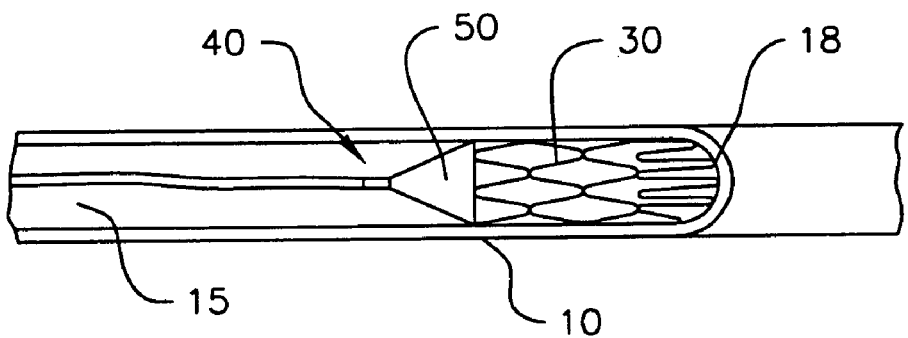
FIG. 2 is an elevation sectional view taken on line 2—2 of FIG. 1.

In stent 30, the filaments shown are wire-forms, and the technique for joining crowns can be welding, brazing or soldering. Polymeric materials can also be used, in which case, adhesive or thermal bonding maybe appropriate joining techniques. Optionally, a flared stent of the invention can be fabricated by etching or laser cutting material from metal or polymeric tubes, or from flat sheets that can be rolled up and joined into tubular forms. Any pattern shape of cells and filaments is feasible according to the invention, as long as the flared or tapered expanded configuration has a substantially uniform pattern density along the length. Stent 30 is shown in FIGS. 1–3 as a balloon-expandable stent, but it may also be self-expandable, in which case, stent 30 would typically be delivered within a retractable sheath (not shown). Self-expandable stents are typically manufactured of pseudo-elastic metals, such as nitinol (NiTi), while balloon expandable stents are more commonly fashioned from metals such as stainless steels (e.g. 316 L, 316 M) or precipitation hardenable alloys (e.g. PH 455).

Figure 6:
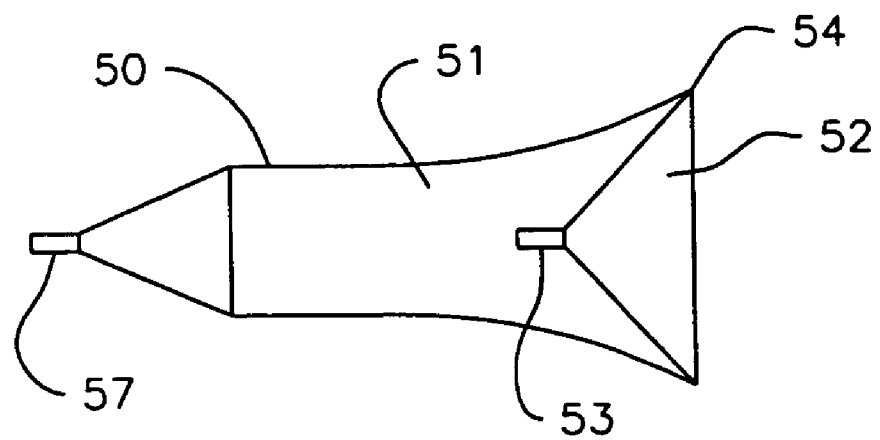
FIG. 6 is an elevation view, in section, of a balloon for a stent system according to the invention, shown in an inflated shape.

FIG. 6 illustrates balloon 50, which is part of a system for delivery of stent 30, as shown in FIG. 1. When balloon 50 is inflated, central body 51 is shaped to generally match the expanded configuration of stent 30. Distal end 52 has a concavity, or an inverted cone, such that distal neck 53 is set back proximally from distal lip 54. Distal neck 53 may also be inverted (not shown) within conical distal end 52. The distal concavity in balloon 50 permits catheter 40 to deploy stent 30 immediately proximal to carina 18, as shown in FIG. 1. The proximal end of balloon 50 tapers conventionally from central body 51 to proximal neck 57. Distal and proximal necks 53, 57 are adapted to be mounted to catheter 40, as will be understood by those skilled in the art of balloon catheters. Balloon 50 can be stretch blow-molded from non-compliant biocompatible thermoplastics, as is common to the arts of balloon forming in PTCA and stent delivery.

While the invention has been particularly shown and described with reference to the several disclosed embodiments thereof, it will be understood by those skilled in the art that various changes in form and detail may be made therein without departing from the spirit and scope of the invention.

We claim:

1. A tubular stent comprising first and second ends and being deformable between compressed and expanded configurations, the compressed configuration having a generally constant diameter and a pattern density adjacent the first end that is greater than a pattern density adjacent the second end, the expanded configuration having a transverse dimension at the first end that is larger than a transverse dimension at the second end and having a pattern density adjacent the first end that is substantially equal to a pattern density adjacent the second end, and wherein, when in the expanded configuration, the first end is flared to a generally oval transverse section and the second end is generally circular in transverse section such that the stent is adapted for implantation proximally abutting a carina of a vessel bifurcation.

2. A stent system comprising the stent of claim 1 and at least one tubular stent element distally abutting the field end of the stent.

3. A stent system comprising the stent of claim 1 mounted, in the compressed configuration, about a balloon inflatably disposed at a distal end of a delivery catheter, the balloon having an inflated shape that is flared to generally match the expanded configuration of the stent.

4. A stent system of claim 3, the inflated shape of the balloon further having an inverted conical distal end.

* * * * *